United States Patent [19]

Minagawa et al.

[11] 4,416,797
[45] Nov. 22, 1983

[54] CHLORINATED ORGANIC COMPOUNDS HAVING THEIR RESISTANCE TO DETERIORATION ENHANCED BY 1,3-DICARBONYL COMPOUNDS

[75] Inventors: Motonobu Minagawa, Kosigaya; Tetsuyu Inoue, Warabi; Naoyasu Kurita, Urawa, all of Japan

[73] Assignee: Adeka Argus Chemical Co., Ltd., Urawa, Japan

[21] Appl. No.: 235,817

[22] Filed: Feb. 19, 1981

[30] Foreign Application Priority Data

Mar. 3, 1980 [JP] Japan .................................. 55-26256
May 19, 1980 [JP] Japan .................................. 55-66081

[51] Int. Cl.³ ............................................. C09K 15/32
[52] U.S. Cl. ............................ 252/400 A; 252/400 R; 252/401; 252/402; 252/403; 252/406; 252/407
[58] Field of Search ............... 570/102, 108; 252/403, 252/400 A, 407, 400 R; 260/45.75 R, 45.85 B, 45.85 T, 32.2, 408; 524/177, 178, 291, 292, 301, 396; 560/51, 53, 54

[56] References Cited

U.S. PATENT DOCUMENTS 3,001,970  9/1961  Ebel .................................. 260/45.7 R
4,102,839  7/1978  Crochemove et al. ....... 260/45.75 R
4,123,399  10/1978  Gay .............................. 260/45.95 L
4,123,400  10/1978  Gay .............................. 260/45.95 L
4,381,360  4/1983  Leistner et al. ................ 252/407 X Primary Examiner—Josephine Barr

[57] ABSTRACT

Chlorinated organic compounds having their resistance to deterioration (when heated, exposed to light or water, or in contact with certain metals such as iron and aluminum) enhanced by a 1,3-dicarbonyl compound having the formula:

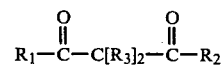

wherein:
$R_1$ is selected from the group consisting of hydrogen, hydrocarbon groups having from one to about eighteen carbon atoms and such groups substituted with one or more groups selected from the group consisting of halogen, hydroxy, alkoxy $OR_1$, ester $COOR_1$, alkyl and alkoxycarbonyl alkyl having from one to about eighteen carbon atoms;

$R_2$ is selected from the group consisting of hydrocarbon groups having from one to about eighteen carbon atoms and such groups substituted with one or more groups selected from the group consisting of halogen, hydroxy, alkoxy $OR_1$, ester $COOR_1$, alkyl and alkoxycarbonyl alkyl having from one to about eighteen carbon atoms;

$R_3$ is selected from the group consisting of hydrogen, hydrocarbon groups having from one to about eighteen carbon atoms and such groups substituted with one or more groups selected from the group consisting of halogen, hydroxy, alkoxy $OR_1$, ester $COOR_1$, alkyl and alkoxycarbonyl having from one to about eighteen carbon atoms; and

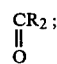

provided, when both $R_3$ are hydrogen, at least one $R_1$ and $R_2$ is other than methyl as well as metal and organotin enolate salts thereof. The compounds are effective in enhancing the resistance to deterioration of chlorinated hydrocarbons and chlorinated higher fatty acid esters.

23 Claims, No Drawings

CHLORINATED ORGANIC COMPOUNDS HAVING THEIR RESISTANCE TO DETERIORATION ENHANCED BY 1,3-DICARBONYL COMPOUNDS

Chlorinated paraffinic hydrocarbons and chlorinated higher fatty acid esters are widely used, for example, as a plasticizer for synthetic and natural resins, such as polyvinyl chloride, vinyl chloride/vinyl acetate copolymers, chlorinated polyethylene, and polyvinylidene chloride; as a flame retardant for thermoplastic resins and rubbers; as extreme pressure additives for cutting oils, gear oils, and bearing oils, as a vehicle for flame retardant coatings; as a flameproofing agent for paper and cloth, and as a plasticizer for printing inks.

Chlorinated hydrocarbons such as trichloroethylene, 1,1,1-trichloroethane, and perchloroethylene have a good solubility for greases, fats and waxes, good flame resistance, and a low boiling point, so that they are widely used as industrial solvents in degreasing, washing, drying, extraction and paint removal. Also, dichloropropane and dichloropropylene are useful as vehicles for insecticides.

These chlorinated organic compounds, however, are unstable and undergo dehydrochlorination when exposed to light, or heat, or in contact with water and certain metals such as iron and aluminum. The hydrogen chloride or chlorine liberated are corrosive, so that processing machinery have been subjected to corrosion, and treated materials are discolored. Many compounds have been used as stabilizers, but none have been fully satisfactory.

Compounds such as epoxy compounds, organotin compounds, lead salts and metal soaps have been used as stabilizers for chlorinated paraffin and higher fatty acid esters. Also, more recently, p-tert-butylcatechol, n-propylacetate, dinonylphthalate, alkaline earth metal hydroxides, and combinations of epoxy compounds and pentaerythritol or magnesium salts have been proposed.

Stabilizers proposed for chlorinated lower hydrocarbons include phenols, such as phenol, cresol, thymol, nitrophenol and eugenol; amines such as diethylamine, triethylamine, hexamethylene tetraamine, cyclohexylamine, dicyclohexylamine, morpholine, piperidine, aniline and pyridine; epoxides such as propylene oxide, butylene oxide, epichlorohydrin and allyglycidyl ether; ethers such as ethyl ether, propyl ether, ethylpropargyl ether, and phenylpropargyl ether; alcohols such as ethyl alcohol, propyl alcohol, butyl alcohol, allyl alcohol, methallyl alcohol, propargyl alcohol, methylpentenol and 3-methyl-1-pentyl-3-ol; esters such as methyl formate, ethyl formate, propargyl formate, propargyl acetate and propargyl benzoate; nitro compounds such as nitromethane and nitroethane; cyano compounds such as ethyl cyanamide, propyl cyanamide and dimethyl cyanamide; azo compounds; imino ethers; carbonates; lactams; and imidazoles. Also, combinations of the above compounds have been proposed. However, none has been satisfactory in enhancing resistance to heat deterioration.

1,3-Dicarbonyl compounds are known stabilizers for halogen-containing resins, but not for chlorinated hydrocarbons or chlorinated higher fatty acid esters.

J. Darby, U.S. Pat. No. 2,669,548, patented Feb. 16, 1954, discloses halogen-containing resin compositions having improved stability containing a mixture of a zinc salt and a calcium chelate derivative of a 1,3-dicarbonylic compound.

F. Ebel, U.S. Pat. No. 3,001,970, patented Sept. 26, 1961, discloses preventing the discoloration of vinylidene chloride polymers by light by adding a small amount of dibenzoyl methane.

British Pat. No. 1,141,971 of May 23, 1967 to W. R. Grace & Co. discloses zinc complexes of beta-dicarbonyl compounds, used as stabilizing additives for chlorine-containing polymers.

L. Weisfeld, U.S. Pat. No. 3,493,536, patented Feb. 3, 1970, discloses that diaroylmethane compounds provide stabilizing action against the sensitizing effect of bismuth or antimony compounds on chlorine-containing materials.

M. Crochemore, U.S. Pat. No. 4,102,839, patented July 25, 1978, discloses the possibility of preventing the thermal breakdown of vinyl chloride polymers by adding one or more metal salts and a 1,3-dicarbonyl compound.

M. Gay, U.S. Pat. Nos. 4,123,399 and 4,123,400, patented Oct. 31, 1978, discloses vinyl chloride compositions containing metal salts, polyol and a 1,3-dicarbonyl compound.

1,3-Dicarbonyl compounds are known that contain carboxy or ester groups, but not as vinyl chloride polymer stabilizers. 1,3-Dicarbonyl compounds containing carboxy or ester groups can be prepared by the base-catalyzed condensation reaction of a diester of benzene dicarboxylic acid with a ketone (see, for example, B. T. Brown et al, *Pestic. Sci.* 1973, 473–484) or by reaction of a carboxy acetophenone with a carboxylic ester (see, for example, H. Imai et al, *Nippon Kagaku Kaishi* 1977, 1081).

In accordance with the present invention, chlorinated organic compounds such as chlorinated hydrocarbons and chlorinated higher fatty acid esters are provided having an enhanced resistance to deterioration by heat due to the presence of a 1,3-dicarbonyl compound having the formula:

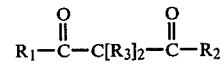

wherein:

R$_1$ is selected from the group consisting of hydrogen, hydrocarbon groups having from one to about eighteen carbon atoms and such groups substituted with one or more groups selected from the group consisting of halogen, hydroxy, alkoxy OR$_1$, ester COOR$_1$, alkyl and alkoxycarbonyl alkyl having from one to about eighteen carbon atoms;

R$_2$ is selected from the group consisting of hydrocarbon groups having from one to eighteen carbon atoms and such groups substituted with one or more groups selected from the group consisting of halogen, hydroxy, alkoxy OR$_1$, ester COOR$_1$, alkyl and alkoxycarbonyl alkyl having from one to about eighteen carbon atoms;

R$_3$ is selected from the group consisting of hydrogen, hydrocarbon groups having from one to about eighteen carbon atoms and such groups substituted with one or more groups selected from the group consisting of halogen, hydroxy, alkoxy OR$_1$, ester COOR$_1$, alkyl and alkoxycarbonyl alkyl having from one to about eighteen carbon atoms; and

provided, when both $R_3$ are hydrogen, at least one of $R_1$ and $R_2$ is other than methyl as well as metal and organotin enolate salts thereof.

One of $R_1$ and $R_2$ can be taken together with one $R_3$ to form a cyclic ring, as in $\alpha$- or $\beta$-tetralone, with the other of $R_1$ and $R_2$ a substituent on the ring, as in acetyl tetralone.

$R_1$ and $R_2$ can be taken together to form a cyclic ring, as in cyclohexane-1,3-dione.

Such bivalent $R_1$, $R_2$ and $R_3$ groups ae encompassed in the definitions of $R_1$, $R_2$ and $R_3$ above, and in the claims.

The 1,3-dicarbonyl compound is employed with such chlorinated organic compounds in an amount within the range from 0.0001 to 10 parts, preferably from 0.001 to 5 parts, per 100 parts by weight of the chlorinated compound.

These compounds also exist in the equilibrium forms of metal and organotin enolate salts of either or both (in admixture) of the two general enol forms:

(assuming one $R_3$ = H)

The metal as in other enolate salts replaces one or more hydrogens of the enol hydroxyls, according to the valence of the metal, producing enolate salts of one or both of the forms:

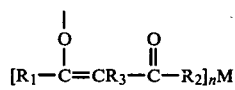 II

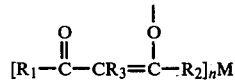 III which salts are accordingly represented generically herein by the formula:

IV

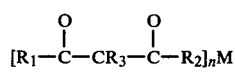

it being understood that one hydrogen is replaced by M at one enol group.

n represents the valence of M. M is any metal, monovalent or polyvalent, preferably a metal conventionally used in metal salt stabilizers for polyvinyl chloride resins, such as lithium, sodium, potassium, magnesium, strontium, barium, calcium, cadmium, lead, zinc, aluminum, antimony, tin or zirconium, as well as organotin $(R)_m$ Sn where m is one, two or three, and R is a hydrocarbon group having from one to about eighteen carbon atoms.

The tautomeric equilibrium between Form I and Forms II and III can be represented as follows:

For the monovalent metal salts M, the equilibrium becomes:

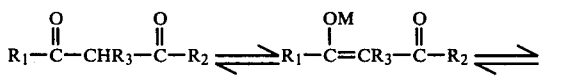

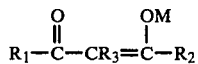

III

For polyvalent metal salts, the 1,3-dicarbonyl radical is multiplied according to the valence of M.

All forms of 1,3-dicarbonyl compounds of this invention are effective in enhancing the resistance to deterioration when subjected to light or heat, or exposed to water or certain metals such as iron and aluminum, of chlorinated organic compounds. When M is a metal, while numerous structural formulae can be written, differing in the location of metal in the enolate, all are equivalent, and therefore the formula is better represented as a hybrid of all formulae than any single one.

The M organotin group has from one to three hydrocarbon groups R linked to tin through carbon. Each hydrocarbon group R linked to carbon can have from one to eighteen carbon atoms. The hydrocarbon groups R include alkyl, cycloalkyl, aryl, and alkaryl groups. The R group can also be substituted with one or more ester groups $COOR_2$. Alkyl groups and alkoxycarbonyl alkyl groups are preferred.

Exemplary R groups include methyl, butyl, hexyl, octyl, isooctyl, 2-ethyl hexyl, nonyl, decyl, stearyl; cyclohexyl, cyclopentyl, cycloheptyl; phenyl, benzyl, phenethyl, naphthyl; methoxycarbonylethyl, ethoxycarbonylmethyl, and butoxycarbonylethyl.

The total of the number of organic groups R linked to tin through carbon plus the number of 1,3-dicarbonyl groups is:

| Type of organotin group: | Monoorganotin RSn | Diorganotin $R_2$Sn | Triorganotin $R_3$Sn |
|---|---|---|---|
| Number of 1,3-dicarbonyl groups: | 3 | 2 | 1 |

The organic groups R linked to tin through carbon can be the same or different.

Representative organotin groups include monomethyltin, mono-n-butyltin, monoisobutyltin, mono-2-ethylhexyltin, methoxycarbonylethyltin; dimethyltin, di-n-butyltin, di(ethoxycarbonylethyl)tin, methyl-n-octyltin, n-butyl-n-butoxycarbonylethyltin, di-n-octyltin; tri(methoxycarbonylethyl)tin, tri-n-octyltin, and methyl di(2-ethylhexyloxycarbonylethyl)tin.

The hydrocarbon groups $R_1$, $R_2$ and $R_3$ can be open chain or cyclic, and include such aliphatic, cycloaliphatic and aromatic hydrocarbon groups as alkyl groups having from one to about eighteen carbon atoms; cycloalkyl, cycloalkylalkylene, and alkylcycloalkyl groups having from five to about eighteen carbon atoms; and aryl groups (including aralkyl and alkaryl groups) having from six to about eighteen carbon atoms; for example, methyl, ethyl, propyl, isopropyl, butyl, isobutyl, sec-butyl, tert-butyl, amyl, tert-amyl, tert-hexyl, tert-heptyl, iso-heptyl, tert-octyl, 2,4,4-trimethylpentyl, 2-ethylhexyl, iso-octyl, nonyl, decyl, dodecyl, tridecyl, tetradecyl, pentadecyl, hexadecyl, heptadecyl, octadecyl; 1-methylcyclopentyl, cyclohexyl, cycloheptyl; phenyl, naphthyl, methylphenyl, ethylphenyl, butylphenyl, t-butylphenyl, octylphenyl, nonylphenyl, dimethylphenyl, benzyl and phenethyl.

Substituted hydrocarbon $R_1$, $R_2$ and $R_3$ groups include trifluoromethyl, trichloromethyl, hydroxyheptadecyl, methoxyethyl, hydroxyphenyl, methoxyphenyl, methylenedioxyphenyl, carbomethoxyphenyl and chlorophenyl.

Particularly preferred 1,3-dicarbonyl compounds represented by the above general formulae according to the invention include the compounds listed below, as well as their enol tautomers, and metal enolates and organotin enolates: dehydroacetic acid, dehydropropionyl acetic acid, dehydrobenzoyl acetic acid, cyclohexane-1,3-dione, dimedone, 2,2'-methylene bis cyclohexane-1,3-dione, 2-benzylcyclohexane-1,3-dione, acetyltetralone, palmitoyltetralone, stearoyltetralone, benzoyltetralone, 2-acetylcyclohexanone, 2-benzoylcyclohexanone, 2-acetylcyclohexane-1,3-dione, benzoyl-p-chlorobenzoylmethane, bis(4-methylbenzoyl) methane, bis(2-hydroxybenzoyl) methane, benzoylacetylmethane, tribenzoylmethane, diacetylbenzoylmethane, stearoylbenzoylmethane, palmitoylbenzoylmethane, lauroylbenzoylmethane, dibenzoylmethane, 4-methoxybenzoyl-benzoylmethane, bis(4-methoxybenzoyl) methane, bis(4-chlorobenzoyl) methane, bis (3,4-methylenedioxybenzoyl)methane, benzoylacetyloctylmethane, benzoylacetylphenylmethane, stearoyl-4-methoxybenzoylmethane, bis(4-t-butylbenzoyl)methane, benzoylacetylethylmethane, benzoyltrifluoroacetylmethane, butanoylacetylmethane, heptanoylacetylmethane, triacetylmethane, stearoylacetylmethane, palmitoylacetylmethane, lauroylacetylmethane, benzoylformylmethane, acetylformylmethane, benzoylphenylacetylmethane, bis(cyclohexanoyl)methane and dipivaloylmethane.

The β-diketone compounds are used in a stabilizing amount within the range from about 0.001 to about 10 parts by weight, preferably from 0.001 to 5 parts by weight, per 100 parts by weight of chlorinated organic compounds.

The 1,3-dicarbonyl compounds are prepared by conventional procedures described in the prior art referred to above.

The β-diketone compounds in accordance with the invention are effective with chlorinated lower hydrocarbons having from one to about six carbon atoms, such as chloromethane, methylene chloride, chloroform, carbon tetrachloride, ethyl chloride, 1,2-dichloroethane, 1,1-dichloroethane, 1,1,1-trichloroethane, 1,1,2-trichloroethane, tetrachloroethane, pentachloroethane, hexachloroethane, monochloropropane, 1,3-dichloropropane, 1,2-dichloropropane, monochlorobutane, dichlorobutane, vinyl chloride, dichloroethylene, trichloroethylene, tetrachloroethylene, chloropropene, 1,3-dichloropropene, dichloropropylene, monochlorobutene, dichlorobutene, 3-chloro-2-methylpropene-1, trichlorobutene, 2-chloro-1,3-butadiene, 2,3-dichlorobutadiene-1,3, dichloroacetyne and 1,1-dichloro-4-methylpento-1,3-diene.

The chlorinated higher hydrocarbons or paraffinic hydrocarbons include chlorinated natural or synthetic n-paraffin, paraffin or paraffin wax having from six to fifty carbon atoms, preferably from ten to forty carbon atoms, and chlorinated aliphatic hydrocarbons and mixtures thereof having one or several double bonds in a molecule having from six to thirty-two carbon atoms. The chlorination may be carried out in any conventional manner, such as that disclosed in Japanese Pat. Nos. 5,531/56, 8,849/67, 14,925/67 and 14,926/67. The chlorine content is preferably within the range from 10 to 80% by weight, preferably from 20 to 70% by weight.

The chlorinated higher fatty acid esters are of (a) saturated and unsaturated fatty acids, having from about ten up to about thirty carbon atoms, such as lauric acid, myristic acid, palmitic acid, stearic acid, arachidic acid, behenic acid, montanic acid, 4-dodecanoic acid, 5-dodecanoic acid, 9-hexadecanoic acid, oleic acid, 11-octadecanoic acid, 9-eicosenoic acid, linoleic acid, and linolenic acid; mixed animal oil fatty acids such as tallow, whale oil and cod liver oil; and mixed plant oil fatty acids such as hempseed oil, linseed oil, olive oil, sesame oil, soybean oil, teaseed oil, rapeseed oil, palm oil, castor oil, cottonseed oil and coconut oil, with (b) alcohols having from one to about thirty carbon atoms, such as methyl, ethyl, propyl, isopropyl, butyl, isobutyl, tert-butyl, amyl, isoamyl, hexyl, heptyl, octyl, isooctyl, 2-ethylhexyl, nonyl, decyl, isodecyl, dodecyl, tetradecyl, hexadecyl, stearyl and behenyl alcohols.

The effectiveness of the 1,3-diketone compounds can be enhanced by including a stabilizer for chlorinated organic compounds. The known stabilizers include epoxy compounds, such as epoxidized soybean oil, epoxidized linseed oil, epoxidized fish oil, epoxidized tall oil fatty acid ester, epoxidized tallow oil, epoxidized polybutadiene, epoxymethyl-, butyl-, 2-ethylhexylstearyl-stearate, tris(epoxypropyl) isocyanurate, epoxidized castor oil, epoxidized safflower oil, epoxidized linseed oil fatty acid butylester, 3-(2-xenoxy)-1,2-epoxypropane, dicyclopentadiene diepoxide, 3,4-epoxycyclohexyl-6-methylepoxycyclohexane carboxylate, butylene oxide, propylene oxide, cyclohexene oxide, phenylglycidyl ether, and epichlorhydrin; polyhyric alcohols such as trimethylolethane, trimethylolpropane, glycerin, 2-hydroxymethyl-3-methylbutane-1,3-diol, 3-methylpentane-1,3,5-triol, tris-(2-hydroxyethyl) isocyanurate, hexane-1,2,6-triol, 2-hydroxymethyl-2-methyl-butane-1,3-diol, 2,4-dimethyl-3-hydroxymethylpentane-2,4-diol, pentaerythritol, diglycerol, ditrimethylolethane, ditrimethylolpropane, 2,2,6,6-tetramethylol cyclohexanol, dipentaerythritol, mannitol, sorbitol and partial esters thereof; alcohols such as isopropyl alcohol, tert-butyl alcohol, s-butyl alcohol, allyl alcohol, methylpentenol, propargyl alcohol, 2-methyl-butyne-2-ol and 1-pentyne-3-ol; aldehydes, such as acetaldehyde, propionaldehyde, and benzaldehyde; ketones such as acetone, acetylacetone and methylethyl ketone; ethers such as diethyl ether, diisopropyl ether, phenylmethyl ether, allyl ethyl ether and ethylene glycol diethyl ether; esters such as ethylacrylate, butylmethacrylate and butylacetate; nitro compounds such as nitromethane and nitroethane; amines such as diisobutylamine, triethylamine, diisopropylamine, cyclohexylamine and diphenylamine; cyclic ethers such as tetrahydrofurane, tetrahydropyrane, 1,4-dioxane, 1,3-dioxane and 1,3,5-trioxane; thymols, morpholines, guaiacols, piperidines, hydrazones, alkylbenzenes, alkylnitriles, aldoximes, caprolactams, carbonates, alkyltin salts, phosphites, dialkyl phosphoric acid alkali metal salts, imidazoles, and thiocyanates.

Also useful are antioxidants such as phenols and sulfur-containing compounds, and UV-absorbers such as benzophenones, benzotriazoles, salicylates, substituted acrylonitriles, Ni or Cr salts or chelates, triazines and piperidines.

The stabilizer system is incorporated in the chlorinated organic compound by simple mixing, using any suitable mixing equipment according to whether the organic compound is liquid, such as a stirred vessel, or solid, in which case the vessel can be heated to melt the compound, or a mill or a Banbury mixer. If the polymer has a melting point which is too high for mixing equipment, a solvent can be worked in until its viscosity has been reduced to the desired range before addition of the stabilizer. Mixing is continued until the mixture is substantially uniform. The resulting composition is then removed from the mixing equipment and brought to the form desired for marketing or use.

The following Examples illustrate preferred β-diketone/chlorinated organic compound compositions of the invention showing the stabilizing effect of the β-diketones or chlorinated lower hydrocarbons, paraffinic hydrocarbons, and chlorinated higher fatty acid esters.

EXAMPLES 1 TO 9

Stabilized chlorinated hydrocarbon compositions were prepared having the following formulation:

| Ingredient | Parts by Weight |
| --- | --- |
| Chlorinated paraffin | 100 |
| (n-Paraffin hydrocarbons having fourteen to fifteen carbon atoms, chlorine content 50%, molecular weight 394) | |
| Epoxidized soybean oil | 0.5 |
| Zn octoate | 0.003 |
| β-Diketone listed in Table I | 0.002 |

The compositions were prepared by mixing the above ingredients. 2 g of the composition was taken in a test tube, and Congo red test paper 7 mm wide and 40 mm long wetted with glycerol was held vertically at the top of the test tube by a wad of refined cotton. The test tube was put in an oil bath heated at 110° C. and the time to develop a blue discoloration was measured.

The results obtained are shown in Table I.

TABLE I

| Example No. | β-Diketone | Time to develop Blue Discoloration (hours) |
| --- | --- | --- |
| | None | Less than 1 |
| 1 | Dibenzoyl methane | 12.5 |
| 2 | Stearoylbenzoyl methane | 10.5 |
| 3 | Dehydroacetic acid | 11.0 |
| 4 | 2-Benzoylcyclohexanone | 9.5 |
| 5 | Benzoylacetylphenyl methane | 10.0 |
| 6 | Lauroylacetylmethane | 10.5 |
| 7 | Bis(4-t-butylbenzoyl)methane | 11.0 |
| 8 | Dehydroacetic acid, Ba salt | 11.5 |
| 9 | Dehydroacetic acid, K salt | 10.0 |

It is apparent that the β-diketones extend the resistance to discoloration to from 9.5 to 12.5 hours.

EXAMPLES 10 TO 17

Stabilized chlorinated ester compositions were prepared by mixing 100 parts by weight of pentachloromethylstearate ester and 2 parts by weight of the β-diketones listed in Table II.

75 g of the composition was taken in a 200 ml flask, heated in an oil bath at 150° C., blowing out hydrogen chloride gas liberated with a stream of nitrogen gas and absorbing the HCl in aqueous sodium hydroxide solution. The amount of HCl absorbed after one hour, two hours and three hours was determined by titration with standard hydrochloric acid, and the amount of liberated hydrogen chloride calculated.

The results obtained are shown in Table II.

TABLE II

| Example No. | β-Diketone | Amount of HCl (mg) After | | |
| --- | --- | --- | --- | --- |
| | | 1 hour | 2 hours | 3 hours |
| | None | 19.6 | 62.1 | 86.9 |
| Control | Epoxidized soybean oil | 2.25 | 6.56 | 10.5 |
| 10 | Lauroylbenzoyl methane | 2.33 | 4.73 | 6.02 |
| 11 | Benzoylacetyloctyl methane | 2.46 | 4.98 | 6.34 |
| 12 | Dibenzoyl methane | 2.60 | 5.27 | 6.70 |
| 13 | Stearoylacetyl methane | 2.64 | 5.34 | 6.80 |
| 14 | Dehydroacetic acid | 2.71 | 5.48 | 6.97 |
| 15 | Dehydrobenzoyl acetic acid | 2.24 | 4.52 | 5.75 |
| 16 | Dibenzoyl methane, Ba salt | 2.55 | 5.16 | 6.57 |
| 17 | Dehydroacetic acid, Mg salt | 2.68 | 5.41 | 6.89 |

The large reduction in HCl liberated as compared to epoxidized soybean oil is apparent from the data, attesting to the greater effectiveness of the β-diketones of the invention.

EXAMPLES 18 TO 31

Stabilized chlorinated paraffin wax compositions were prepared using a combination of two stabilizers and having the following formulation:

| Ingredient | Parts by Weight |
| --- | --- |
| Chlorinated paraffin wax | 100 |
| (twenty to twenty-four carbon atoms, chlorine content of 40%) | |
| β-Diketone listed in Table III | 0.01 |
| Second stabilizer listed in Table III | 2.0 |

The compositions were prepared by mixing the above ingredients. 2 g of the composition was taken in a test tube, and Congo red test paper 7 mm wide and 40 mm long wetted with glycerol was held vertically at the top of the test tube by a wad of refined cotton. The test tube was put in an oil bath heated at 100° C. and the time to develop a blue discoloration was measured.

The results obtained are shown in Table III.

TABLE III

| Example No. | β-Diketone | Second Stabilizer | Time to Develop Blue Discoloration (hours) |
| --- | --- | --- | --- |
| 18 | Dibenzoyl methane | Epoxidized soybean oil | 11.5 |
| 19 | Dibenzoyl methane | Epoxidized methyl stearate | 10.0 |
| 20 | Dibenzoyl methane | Pentaerythritol | 10.5 |

TABLE III-continued

| Example No. | β-Diketone | Second Stabilizer | Time to Develop Blue Discoloration (hours) |
|---|---|---|---|
| 21 | Stearoylbenzoyl methane | Epoxidized linseed oil | 11.0 |
| 22 | Stearoylbenzoyl methane | Vinyl cyclohexene diepoxide | 9.0 |
| 23 | Stearoylbenzoyl methane | Bisphenol A diglycidyl ether | 9.5 |
| 24 | Dehydroacetic acid | Epoxidized soybean oil | 10.0 |
| 25 | Dehydroacetic acid | Dicyclopentadiene diepoxide | 10.0 |
| 26 | Dehydroacetic acid, Ba salt | Diglycerol | 9.5 |
| 27 | Dehydroacetic acid, Ba salt | Tris(epoxypropyl) isocyanurate | 9.5 |
| 28 | Dehydroacetic acid, Zn salt | Epoxidized butadiene | 11.0 |
| 29 | Dehydroacetic acid, Zn salt | Pentaerythritol | 10.5 |
| 30 | Dibenzoyl methane | 1:1 Mixture of epoxidized soybean oil and pentaerythritol | 12.0 |
| 31 | Dibenzoyl methane | 1:1 Mixture of epoxidized soybean oil and trimethylolpropane | 11.5 |

Comparison of Examples 1, 2, 3 and 8 (Table I) with the above results shows the enhanced effectiveness imparted by the second stabilizer.

EXAMPLES 32 TO 39

Into a flask equipped with condenser and CaCl₂ drying tube was charged 100 ml of perchloroethylene and 0.01 part by weight of the β-diketone or Control compound listed in Table IV. One piece of well-polished mild steel was then placed in the liquid, while another piece was hung 3 cm above the surface of the mixture in the flask.

The flask was then heated by a mantle heater to reflux the perchloroethylene. After twenty-four hours, the steel specimens were taken out and washed, and the surface of the steel and the color of perchloroethylene were noted for corrosion of the steel. The results are shown in Table IV.

The corrosion is rated by + on a scale where the greater the number of +, the greater the corrosion. Absence of corrosion is indicated by −.

TABLE IV

| | | After 24 hours Corrosion of steel sample | | |
|---|---|---|---|---|
| Example No. | Stabilizer | Immersed in Liquid | Bathed in Vapor over liquid | Color |
| Control 1 | None | +++++++ | ++++++ | Tar |
| Control 2 | Ethanol | +++++ | +++ | Yellow |
| Control 3 | Thymol | ++++ | +++ | Yellow |
| Control 4 | Propargyl alcohol | ++++ | ++ | Dark yellow |
| Control 5 | sec-Butyl alcohol | +++++ | +++ | Dark yellow |
| Control 6 | Diisobutyl amine | ++++ | +++ | Brown |
| Control 7 | 1,4-Dioxane | +++ | ++ | Dark yellow |
| Control 8 | Butylene oxide | +++ | ++ | Brown |
| 32 | Dehydroacetic acid | + | − | Normal shiny |
| 33 | 2-Benzylcyclohexane 1,3-dione | + | − | Normal shiny |
| 34 | Benzoylacetyl methane | − | − | Normal shiny |
| 35 | Dibenzoyl methane | − | − | Normal shiny |
| 36 | Stearoylbenzoyl methane | − | − | Normal shiny |
| 37 | Benzoyltetralone | + | − | Normal shiny |
| 38 | Lauroylacetyl methane | − | − | Normal shiny |
| 39 | Dibenzoyl methane, Zn salt | − | − | Normal shiny |

The improved effectiveness of the β-diketones compared to the Controls is apparent from the above data.

EXAMPLES 40 TO 50

Into a flask equipped with condenser and CaCl₂ drying tube was charged 1,1,1-trichloroethane and 0.01 part by weight of the β-diketone or Control compound listed in Table V. One piece of well-polished mild aluminium was then placed in the liquid, while another piece was hung 3 cm above the surface of the mixture in the flask.

The flask was then heated by a mantle heater to reflux the trichloroethane. After twenty-four hours, the aluminum specimens were taken out and washed, and the surface of the aluminum and the color of trichloroethane were noted for corrosion of the aluminum. The results are shown in Table V.

The corrosion is rated by + on a scale where the greater the number of +, the greater the corrosion. Absence of corrosion is indicated by −.

TABLE V

| | | After 24 hours Corrosion of aluminum sample | | |
|---|---|---|---|---|
| Example No. | Stabilizer | Immersed in Liquid | Bathed in Vapor over liquid | Color |
| Control 1 | 1,4-Dioxane | +++++ | ++++ | Yellow |

TABLE V-continued

| Example No. | Stabilizer | After 24 hours Corrosion of aluminum sample | | |
|---|---|---|---|---|
| | | Immersed in Liquid | Bathed in Vapor over liquid | Color |
| Control 2 | Propargyl alcohol | ++++ | +++ | Yellow brown |
| Control 3 | Methylethyl ketone | +++++ | +++ | Brown |
| Control 4 | Nitromethane | ++++ | +++ | Brown |
| Control 5 | t-Amyl alcohol | +++++ | ++ | Brown |
| Control 6 | Morpholine | +++ | ++ | Brown |
| 40 | Stearoylbenzoyl methane | + | − | Normal shiny |
| 41 | Dibenzoyl methane | − | − | Normal shiny |
| 42 | Benzoylacetyl methane | + | − | Normal shiny |
| 43 | Dehydroacetic acid | + | − | Normal shiny |
| 44 | Dehydropropionyl acetic acid | ++ | + | Pale yellow |
| 45 | 2-Acetyl cyclohexanone | ++ | + | Pale yellow |
| 46 | Lauroylbenzoyl methane | + | − | Normal shiny |
| 47 | Dehydroacetic acid, Zn salt | − | − | Normal shiny |
| 48 | Dibenzoyl methane, Zn salt | − | − | Normal shiny |
| 49 | Palmitoylbenzoyl methane, K salt | − | − | Normal shiny |
| 50 | Dehydroacetic acid, Ba salt | − | − | Normal shiny |

The improved effectiveness of the β-diketones compared to the Controls is apparent from the above data.

EXAMPLES 51 TO 64

Into a flask equipped with condenser and $CaCl_2$ drying tube was charged the chlorinated hydrocarbon and 0.01 part by weight of the β-diketone or Control compound listed in Table VI. One piece of well-polished mild steel was then placed in the liquid, while another piece was hung 3 cm above the surface of the mixture in the flask.

The flask was then heated by a mantle heater to reflux the chlorinated hydrocarbon. After twenty-four hours, the steel specimens were taken out and washed, and the surface of the steel and the color of the chlorinated hydrocarbon were noted for corrosion of the steel.

The results are shown in Table VI.

TABLE VI

| Example No. | Chlorinated Hydrocarbon | Stabilizer (parts by weight) | Color |
|---|---|---|---|
| 51 | Methyl Chloride | Stearoylbenzoyl methane 0.003 | Normal shiny |
| 52 | Chloroform | Dibenzoyl methane 0.005 | Normal shiny |
| 53 | 1,1-Dichloroethane | Dibenzoyl methane 0.005 | Normal shiny |
| 54 | 1,1-Dichloroethane | Dehydroacetic acid 0.005 | Pale yellow |
| 55 | 1,1,1-Trichloroethane | Dibenzoyl methane 0.001 t-Butyl alcohol 0.005 | Normal shiny |
| 56 | 1,1,1-Trichloroethane | Stearoylbenzoyl methane 0.001 1,4-Dioxane 0.01 | Normal shiny |
| 57 | 1,1,2,2-Tetrachloroethane | Palmitoyltetralone 0.002 Morpholine 0.01 | Normal shiny |

TABLE VI-continued

| Example No. | Chlorinated Hydrocarbon | Stabilizer (parts by weight) | Color |
|---|---|---|---|
| 58 | 1,1,2,2-Tetrachloroethane | Dehydroacetic acid 0.005 Nitromethane 0.005 | Normal shiny |
| 59 | 1,1,2,2-Tetrachloroethane | Dehydroacetic acid 0.001 Epichlorhydrin 0.01 | Normal shiny |
| 60 | 1,1-Dichloroethylene | Dibenzoyl methane 0.01 | Normal shiny |
| 61 | Perchloroethylene | Dibenzoyl methane 0.001 Thymol 0.02 | Normal shiny |
| 62 | Perchloroethylene | Dibenzoyl methane 0.001 Ethanol 0.05 | Normal shiny |
| 63 | Perchloroethylene | Stearylbenzoyl methane 0.001 Triethylamine 0.03 | Normal shiny |
| 64 | 1,2-Dichloro propane | Dibenzoyl methane 0.001 | Normal shiny |

The improved effectiveness of the β-diketones compared to the Controls is apparent from the above data.

Having regard to the foregoing disclosure, the following is claimed as the patentable and inventive embodiments thereof:

1. A chlorinated organic compound having an enhanced resistance to deterioration, comprising a chlorinated organic compound selected from the group consisting of chlorinated hydrocarbons having from one to about fifty carbon atoms and chlorinated higher fatty acid esters having from ten to about thirty carbon atoms and an effective amount of a 1,3-dicarbonyl compound having the formula:

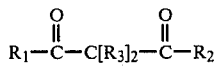

wherein:
- R₁ is selected from the group consisting of hydrogen, hydrocarbon groups having from one to about eighteen carbon atoms and such groups substituted with one or more groups selected from the group consisting of halogen, hydroxy, alkoxy OR₁, ester COOR₁, alkyl and alkoxycarbonyl alkyl having from one to about eighteen carbon atoms;
- R₂ is selected from the group consisting of hydrocarbon groups having from one to about eighteen carbon atoms and such groups substituted with one or more groups selected from the group sisting of halogen, hydroxy, alkoxy OR₁, ester COOR₁, alkyl and alkoxycarbonyl alkyl having from one to about eighteen carbon atoms; and
- R₃ is selected from the group consisting of hydrogen, hydrocarbon groups having from one to about eighteen carbon atoms and such groups substituted with one or more groups selected from the group consisting of halogen, hydroxy, alkoxy OR₁, ester COOR₁, alkyl and alkoxy carbonyl alkyl having from one to about eighteen carbon atoms; and

provided, when both R₃ are hydrogen, at least one of R₁ and R₂ is other then methyl.

2. A chlorinated organic compound according to claim 1 in which the 1,3-dicarbonyl compound is a metal enolate salt of a 1,3-dicarbonyl compound.

3. A chlorinated organic compound according to claim 2 in which the metal is an alkali metal.

4. A chlorinated organic compound according to claim 2 in which the metal is an alkaline earth metal.

5. A chlorinated organic compound according to claim 2 in which the metal is a polyvalent metal.

6. A chlorinated organic compound according to claim 2 in which the metal is selected from the group consisting of lithium sodium, potassium, magnesium, strontium, calcium, barium, cadmium, lead, zinc, tin, aluminum, antimony and zirconium.

7. A chlorinated organic compound according to claim 1 in which both R₃ are hydrogen.

8. A chlorinated organic compound according to claim 1 in which one R₃ is hydrogen and the other is acyl.

9. A chlorinated organic compound according to claim 1 in which R₁ and R₂ are each aryl.

10. A chlorinated organic compound according to claim 9 in which R₁ and R₂ are each phenyl.

11. A chlorinated organic compound according to claim 1 in which R₁ and R₂ are each alkyl.

12. A chlorinated organic compound according to claim 1 in which R₁ is aryl and R₂ is alkyl.

13. A chlorinated organic compound according to claim 1 in which the dicarbonyl compound is dibenzoylmethane.

14. A chlorinated organic compound according to claim 1 in which the dicarbonyl compound is stearoyl benzoylmethane.

15. A chlorinated organic compound according to claim 1 in which the dicarbonyl compounds is dehydroacetic acid.

16. A chlorinated organic compound according to claim 1 in which the dicarbonyl compound is an enol salt of dehydroacetic acid.

17. A chlorinated organic compound according to claim 1 in which the dicarbonyl compound is lauroyl acetylmethane.

18. A chlorinated organic compound according to claim 1 in which the chlorinated organic compound is a chlorinated lower hydrocarbon having from one to about six carbon atoms.

19. A chlorinated organic compound according to claim 1 in which the chlorinated organic compound is a chlorinated paraffinic hydrocarbon having from six to fifty carbon atoms.

20. A chlorinated organic compound according to claim 1 in which the chlorinated organic compound is a chlorinated aliphatic hydrocarbon having from one to several double bonds and from six to thirty-two carbon atoms.

21. A chlorinated organic compound according to claim 1 in which the chlorinated organic compound is a chlorinated higher fatty acid ester of a fatty acid having from about ten up to about thirty carbon atoms, with an alcohol having from one to about thirty carbon atoms.

22. A stabilizer composition capable of enhancing the resistance to deterioration of chlorinated organic compounds, comprising a 1,3-dicarbonyl compound in accordance with claim 1, dand an additional stabilizer for chlorinated organic compounds.

23. A stabilizer composition according to claim 22 in which the additional stabilizer is selected from the group consisting of epoxy compounds; polyhydric alcohols; alcohols; aldehydes; ketones; aliphatic ethers; esters; nitro compounds; amines; heterocyclic ethers; hydrazones, alkylbenzenes, alkylnitryls, aldoximes, caprolactams, carbonates, alkyltin salts, phosphites, dialkyl phosphoric acid alkali metal salts, imidazoles, thiocyanates, phenolic antioxidants and sulfur-containing antioxidants.

* * * * *